(12) United States Patent
Khavinson et al.

(10) Patent No.: US 7,662,789 B2
(45) Date of Patent: Feb. 16, 2010

(54) PEPTIDE SUBSTANCE RESTORING MYOCARDIUM FUNCTION

(75) Inventors: Vladimir Khatskelevich Khavinson, St. Petersburg (RU); Galina Anatolievna Ryzhak, St. Petersburg (RU); Evgeny Iosifovich Grigoriev, St. Petersburg (RU); Irina Yurievna Ryadnova, St. Petersburg (RU)

(73) Assignee: "Access Bioscience" CJSC, Saint-Petersburg (RU)

( * ) Notice: Subject to any disclaimer, the term of this patent is extended or adjusted under 35 U.S.C. 154(b) by 594 days.

(21) Appl. No.: 11/570,482

(22) PCT Filed: Dec. 7, 2004

(86) PCT No.: PCT/RU2004/000493

§ 371 (c)(1), (2), (4) Date: Dec. 12, 2006

(87) PCT Pub. No.: WO2006/001728

PCT Pub. Date: Jan. 5, 2006

(65) Prior Publication Data

US 2008/0269141 A1    Oct. 30, 2008

(30) Foreign Application Priority Data

Jun. 22, 2004    (RU) .............................. 2004118699

(51) Int. Cl.
A61K 38/07    (2006.01)
C07K 5/04    (2006.01)

(52) U.S. Cl. .......................................... 514/18; 530/330

(58) Field of Classification Search ...................... None
See application file for complete search history.

(56) References Cited

FOREIGN PATENT DOCUMENTS

RU    2032422 C1    4/1995
RU    1417242 A1    10/1995

OTHER PUBLICATIONS

Actovegin, *Register of Pharmaceutical Substances of Russia, Drug Encyclopedia*, Moscow, 2003, pp. 63-64.
Amlodipine, *Register of Pharmaceutical Substances of Russia, Drug Encyclopedia*, Moscow, 2003, p. 90.
Dalargin, *Register of Pharmaceutical Substances of Russia, Drug Encyclopedia*, Moscow, 2003, p. 249.
Dobutamin, *Register of Pharmaceutical Substances of Russia, Drug Encyclopedia*, Moscow, 2003, p. 296.
Dopamine, *Register of Pharmaceutical Substances of Russia, Drug Encyclopedia*, Moscow, 2003, pp. 304-305.
Felodipine, *Register of Pharmaceutical Substances of Russia, Drug Encyclopedia*, Moscow, 2003, pp. 865-866.
Isosorbide, *Register of Pharmaceutical Substances of Russia, Drug Encyclopedia*, Moscow, 2003, p. 332.
Nitromint, *Register of Pharmaceutical Substances of Russia, Drug Encyclopedia*, Moscow, 2003, p. 587.
Nitrosorbide, *Register of Pharmaceutical Substances of Russia, Drug Encyclopedia*, Moscow, 2003, p. 588.
Pindolol, *Register of Pharmaceutical Substances of Russia, Drug Encyclopedia*, Moscow, 2003, pp. 659-660.
Propranolol, *Register of Pharmaceutical Substances of Russia, Drug Encyclopedia*, Moscow, 2003, pp. 700-701.
Verapamil, *Register of Pharmaceutical Substances of Russia, Drug Encyclopedia*, Moscow, 2003, p. 180.
Anisimov Sergey V. et al: "Elucidation of the effect of brain cortex tetrapeptide Cortagen on gene expression in mouse heart by microarray," Neuro Endocrinology Letters, Feb.-Apr. 2004, vol. 25, No. 1-2, Feb. 2004, XP009046092, ISSN: 0172-780X—Abstract.
Database Biosis 'Online! Biosciences Information Service, Philadelphia, PA, US; 1992, Bakhtizina G. Z. et al: "Correction of tetramethylthiuram disulfide-induced damage to the myocardium by cardiac peptides," XP002326898, Database accession No. PREV199395091835 abstract, and Patologicheskaya Fiziologiya i Eksperimental 'Naya Terapiya, vol. 0, No, 2, 1992, pp. 27-30, ISSN: 031-2991.
International Searching Authority, International Search Report and Written Opinion for International Application No. PCT/RU2004/000493 dated May 2, 2005.
Pavlenko V. S. (Reprint); Andreeva, L. I.; Ershov V. I.; Khavinson, V. K., Khlystov, V. V.: "Correlation between dose and pharmacological effects of cardiac peptides," Bulletin of Experimental Biology and Medicine, vol. 114, No. 8, 1992, pp. 1144-1147, XP009046094.
Usynin, A. F. et al., "Ischemic myocardium damage and the influence of certain pharmacological substances on it in experimental rats," Urgent Problems of Cardiology, Issue 2—Tomsk, Tomsk University Publishing, 1987, p. 116-118 (rus.).

*Primary Examiner*—Andrew D Kosar
(74) *Attorney, Agent, or Firm*—Leydig, Voit & Mayer, Ltd

(57) ABSTRACT

The invention refers to the pharmaceutical means for the treatment of cardiovascular diseases and can be used as a substance restoring myocardium function in the course of treatment for different forms of this pathology.

There is proposed a new tetrapeptide alanyl-glutamyl-aspartyl-arginine with general formula: Ala-Glu-Asp-Arg sequence 1 [SEQ ID NO:1], revealing biological activity, which is manifested in the restoration of the myocardium function.

There is proposed a pharmacological substance containing an effective amount of tetrapeptide alanyl-glutamyl-aspartyl-arginine with general formula: Ala-Glu-Asp-Arg sequence 1 [SEQ ID NO:1] as an active peptide agent, revealing biological activity, which is manifested by the restoration of myocardium function. Being included in the medication, this substance contributes to the restoration of the myocardium function.

12 Claims, No Drawings

PEPTIDE SUBSTANCE RESTORING MYOCARDIUM FUNCTION

The invention is related to medicinal means of treatment for cardiovascular diseases and can be used as a means of myocardium function restoration in the therapy of different forms of this pathology.

At present the problem of prevention and therapy of cardiovascular diseases remains actual due to the severity and widespread of the latter. A tendency has been revealed towards the increased development of cardiovascular pathology, which stipulates earlier disablement and mortality. In this connection the development of new medicinal substances for the therapy of cardiovascular diseases is of ever growing public concern.

The most widespread forms of cardiac pathology are related to heart ischemia, which occurs as a result of vascular system disturbances and in its severe forms may cause myocardium infarction—the leading cause of death in present-day society. Ischemic heart disease often leads to such complications as disturbed myocardium contraction, excitement and conductive ability. Besides that, one ought to distinguish a separate group of cardiac muscle diseases, the therapy of which is limited mainly to general strengthening therapy and is largely symptomatic. These diseases include myocardium dystrophies, myopathies and cardiomyopathies.

Among the means of myocardium ischemia prevention there are pharmacological substances of different groups, including antagonists for calcium: amlodipin, verapamil, felodipin (Register of Pharmaceutical Substances of Russia. Drug Encyclopedia—Moscow, 2003.—p. 90, p. 180, p. 865 (rus.) and beta adrenoblockators, like propanolol, pindolol (Register of Pharmaceutical Substances of Russia. Drug Encyclopedia—Moscow, 2003.—p. 700, p. 659 (rus.). A peculiarity of action of these substances consists in the reduction of myocardium need for oxygen, as well as a negative inotropic effect. Another class of widely applied preparations is represented by nitrous preparations (different forms of nitrosorbid and mononitrate, clean aerosol nitroglycerine form preparation—nitromint) (Register of Pharmaceutical Substances of Russia. Drug Encyclopedia—Moscow, 2003.—p. 588, p. 332, p. 587) Aside from these preparations one may also use natural or synthetic cardiac glycosides (preparations of *Digitalis L., Strophanthus, Convallaria L.*) (M.D. Mashkovskij. Medicinal preparations. Moscow, Novaya Volna. 2004.—p. 215 (rus.)). Alongside with cardiac glycosides heart activity can be enhanced by non-glycoside cardiotonics. Cardiotonics include sympathomimetic (adrenergic) preparations dobutamine and dopamine (Register of Pharmaceutical Substances of Russia. Drug Encyclopedia—Moscow, 2003.—p. 296, p. 305 (rus.). Certain cardiotonic properties are revealed by substances exerting general positive effect on metabolic processes in the organism.

These preparations have a drawback—they exert side effects and have contraindications. In particular, the majority of such preparations exert a suppressive effect on myocardium sensitivity to excitation, induce arrhythmias, heart failures, hypotonia, bradicardia, as well as cancellation syndrome.

Among known medicinal preparations used for therapy of myocardium ischemia it is necessary to mention actovegin (Register of Pharmaceutical Substances of Russia. Drug Encyclopedia—Moscow, 2003.—p. 63 (rus.) as a preparation effective on cell metabolism and improving energy dependent metabolic processes in the tissues, however its activity is non-specific.

There are known peptide preparations, which exert an effect on myocardium function. They include opioid peptides (A. F. Usynin, V. S. Pavlenko, V. V. Khlystov. Ischemic myocardium damage and the influence of certain pharmacological substances on it in experimental rats. Actual Issues of Cardiology. Issue 2—Tomsk, Tomsk University Publishing, 1987.—p. 116-118 (rus.) and dalargin, their synthetic analogue (Register of Pharmaceutical Substances of Russia. Drug Encyclopedia—Moscow, 2003.—p. 249 (rus.).

Dalargin is known to be applied for the therapy of myocardium infarction as a means of heart ventricles' fibrillations prevention (RU patent No. 2032422 <<Method of myocardium infarction therapy>>, MKI$^6$ A61K38/00, 1995). Moreover, there is known a substance, which enables the improvement of the functional status of the myocardium by means of metabolic disturbances correction based on combined application of dalargin and solcoseryl (RU patent No. 2061484 <<Method of myocardium infarction therapy on its acute stage>>, MKI$^6$ A61K35/14, A61K38/33, 1996).

Cordialin, a standardized complex of low-molecular peptides from the heart is known to have a cardioprotective effect in the restoration period when it is administered after an agricultural poison, TMTD, which causes damages to the cardiomyocytes (Database Biosis, Database accession no PREV/199395091835).

There is also known a polypeptide preparation (RU patent No. 1417242 for the invention "Method of obtainment of the substance restoring myocardium function", MKI A 61K 35/24, 1989), obtained from animal heart and revealing similar biological activity, which is the closest analogue, serving as a prototype for a pharmacological means (pharmaceutical composition).

However, this preparation's application is limited due to the complex method of its obtaining, low active substances yield, significant variability of their physical and chemical properties, as well as due to the possibility of side effects in the form of allergic reactions.

It is noteworthy that the claimed peptide substance—tetrapeptide—does not have any analogues in terms of structure.

The claimed invention is intended to obtain a new biologically active substance of peptide nature restoring myocardium function.

The technical result of the invention consists in the creation of a new peptide substance, as well as of the pharmacological preparation (pharmaceutical composition), containing this peptide substance as an active peptide agent, which, being included in the medication, contributes to the restoration of myocardium function.

The possibility of objective attainment of the technical result while using the invention has been confirmed by reliable data displayed in the examples, which contain experimental data, obtained with respect to the method standardized in this field.

This invention refers to the new tetrapeptide alanyl-glutamyl-aspartyl-arginine with general formula Ala-Glu-Asp-Arg sequence 1 [SEQ ID NO:1].

The tetrapeptide is obtained using classical method of peptide synthesis in the solution (Jacubke H-D., Eschkeit H. Amino acids, peptides, proteins. Transl. from German—Moscow, Mir Publishing Company, 1985—456 p.).

This invention refers to tetrapeptide alanyl-glutamyl-aspartyl-arginine with general formula Ala-Glu-Asp-Arg sequence 1 [SEQ ID NO:1], revealing biological activity, consisting in the restoration of myocardium function.

The activity of tetrapeptide Ala-Glu-Asp-Arg (SEQ ID NO:1), aimed at the restoration of myocardium function, was revealed in the course of its study in case of experimental pathology, in particular when using the following patterns:

Effect of the tetrapeptide on the course of experimental myocardium infarction in case of coronary artery vasoligation in rats;

Effect of the tetrapeptide on the status of isolated heart in case of perfusion and ischemia;

Effect of the tetrapeptide on the course of adrenalin dystrophy in rat myocardium;

Detection of protective activity of the tetrapeptide in case of experimental toxicochemical myocardiopathies;

Effect of the tetrapeptide on the development and outcome of chlorine-calcium arrhythmia in rats;

Effect of the tetrapeptide on the growth of organotypic cardiac culture explants of pubertal rats;

Effect of the tetrapeptide on cardiomyocyte bioenergetics.

It is known that the above described pathologies are characterized by the formation of cardiomyocyte necrosis zones, unbalanced oxygen dependent reactions in the myocardium: biological oxidation processes with growing energy deficit, the increased expenditure of macroergic compounds, the accumulation of insufficiently oxidated compounds, lipid peroxide oxidation products. Calcium transfer and metabolism are disturbed, as well as the distribution of the latter among cellular pools and intercellular space. The observed changes lead to the disturbance in contractive function of the myocardium, as well as to arrhythmia, and cause the development of cardiovascular pathology.

Experimental study showed that Ala-Glu-Asp-Arg (SEQ ID NO:1) tetrapeptide is non-toxic.

This invention also refers to the pharmacological preparation (pharmaceutical composition) restoring myocardium function and containing an effective amount of tetrapeptide alanyl-glutamyl-aspartyl-arginine as its active base, with general formula Ala-Glu-Asp-Arg sequence 1 [SEQ ID NO:1].

The notion "pharmacological means (substance)" under this patent implies the use of such medicinal form containing the effective amount of tetrapeptide with general formula Ala-Glu-Asp-Arg (SEQ ID NO:1), which may find a prophylactic and/or therapeutic use in medicine as a preparation restoring myocardium function.

The notion "effective amount" under this claim implies the use of such a quantity of active peptide base, which in compliance with the quantitative indices of its activity and toxicity, as well as with respect to the knowledge available, shall be effective in this drug form.

In order to obtain necessary pharmaceutical compositions meeting this invention, the suggested tetrapeptide is mixed as an active ingredient with pharmaceutically acceptable carrier according to compounding methods used in pharmaceutics.

The carrier may have different forms, which depend on the pharmaceutical form of the preparation, which must be administered into the organism, for example, parenterally or orally.

Known pharmaceutical components may be used in the process of production of the compositions in the preferred dosage for oral administration.

In case of parenteral administration the carrier usually includes sterile 0.9% sodium chloride solution or sterile water, although other ingredients, which contribute to the preparation's stability, may as well be included.

The subject matter of the invention is explained by tables.

Table 1 shows the effect of Ala-Glu-Asp-Arg (SEQ ID NO:1) tetrapeptide on biochemical indices in rat myocardium in case of experimental infarction (treatment variant).

Table 2 shows the effect of Ala-Glu-Asp-Arg (SEQ ID NO:1) tetrapeptide on the status of isolated guinea pig heart (treatment variant).

Table 3 shows the effect of Ala-Glu-Asp-Arg (SEQ ID NO:1) tetrapeptide on the indices of contractive ability of isolated rat heart after ischemia.

Table 4 shows the effect of Ala-Glu-Asp-Arg (SEQ ID NO:1) tetrapeptide on the indices of peroxide lipid oxidation in rat myocardium in case of adrenalin dystrophy 24 hours after its induction.

Table 5 shows the effect of Ala-Glu-Asp-Arg (SEQ ID NO:1) tetrapeptide on dehydrogenase activity and glycogen content in rat myocardium in 4 hours after adrenalin dystrophy.

Table 6 shows the effect of Ala-Glu-Asp-Arg (SEQ ID NO:1) tetrapeptide on cytomorphologic indices in myocardium in case of rat poisoning with tetramethyl thiuram disulfide.

Table 7 shows the effect of Ala-Glu-Asp-Arg (SEQ ID NO:1) tetrapeptide on the indices reflecting development and outcome of chlorine calcium anemia in rats.

Table 8 shows the effect of Ala-Glu-Asp-Arg (SEQ ID NO:1) tetrapeptide on the growth of organotypic myocardium tissue explants.

Table 9 shows the effect of Ala-Glu-Asp-Arg (SEQ ID NO:1) tetrapeptide on morphological and biochemical indices of guinea pig peripheric blood.

This invention is illustrated by an example of synthesis of the tetrapeptide with formula Ala-Glu-Asp-Arg (SEQ ID NO:1) (Example 1), by examples, confirming biological activity of the tetrapeptide (examples 2, 3, 4, 5, 6, 7, 8), by an example of tetrapeptide toxicity test (example 9), which demonstrate its pharmacological properties and confirm therapeutic activity of the pharmaceutical composition.

EXAMPLE 1

Synthesis of Ala-Glu-Asp-Arg (SEQ ID NO:1) Tetrapeptide

1. Product name: L-alanyl-L-glutamyl-L-aspartyl-L-arginine
2. Structural formula: H-Ala-Glu-Asp-Arg (SEQ ID NO:1)-OH

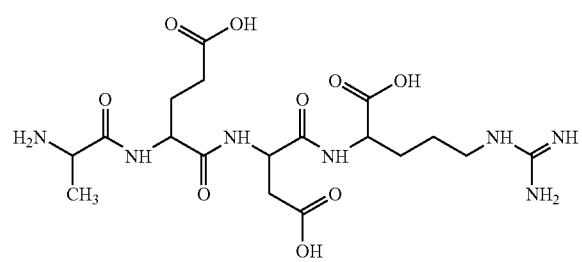

3. Molecular formula without ion pair: $C_{18}H_{31}N_7O_9$
4. Molecular weight without ion pair: 489,48
5. Ion pair: acetate
6. Appearance: white amorphous powder without smell
7. Method of synthesis: the peptide is obtained by a classical method of synthesis in a solution by the following scheme:

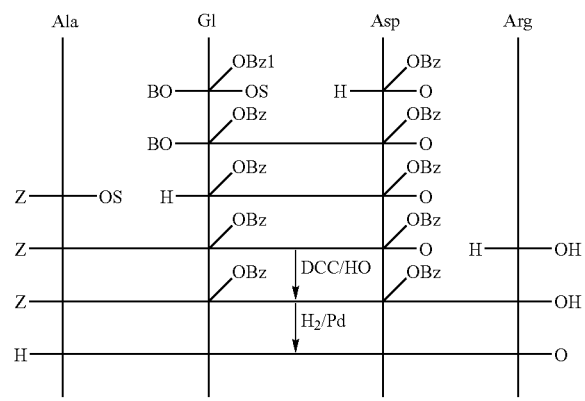

Z—benzyloxycarbonyl group;
BOC—tert.butyloxycarbonyl group;
OSu—N-oxysuccinimide ester;
OBzl—benzyl ester;
DCC—N,N'-dicyclohexylcarbodiimide;
HOBT—N-oxybenzotriazol.

N,N'-dimethylformamide is used as a solvent. When adding aspartic acid, the defence of α-COOH group is applied by salification with triethylamine. BOC-protecting group is removed with trifluoracetic acid (TFA) solution and Z-protecting group—with catalytic hydrogenation. The product is isolated and purified by the method of preparative high-performance liquid chromatography (HPLC) on a reversed phase column.

8. Properties of the finished product:
   amino acid analysis: Glu 1.08; Asp 1.08; Ala 1.00; Arg 1.07;
   peptide content 98.01% (by HPLC, 220 nm);
   TLC—individual, $R_f$=0.59 (acetonitrile-acetic acid-water 5:1:3);
   Moisture content: 8%;
   pH of 0.001% solution: 4.58;
   a specific rotary power: $[\alpha]_D^{22}$: −24° (c=1, H$_2$O).

Example of Synthesis:

1) BOC-Glu(OBzl)-Asp(OBzl)-OH (I), N-tert.butyloxycarbonyl-(γ-benzyl)-glutamyl-(β-benzyl)-aspartate 4.34 g (0.01 mole) of N-oxysuccinimide ester of N-tert.butyloxycarbonyl-(γ-benzyl)glutamic acid BOC-Glu(OBzl)-OSu is dissolved in 20 ml of dimethylformamide, and added with 1.72 ml (0.0125 mole) of triethylamine and 2.80 g (0.0125 mole) of β-benzyl aspartate. The mixture is stirred for 24 hours at room temperature.

Afterwards the product is precipitated with 0.5 N sulphuric acid solution (150 ml), extracted by ethyl acetate (3×30 ml), washed in 0.5 N sulphuric acid solution (2×20 ml), water, 5% sodium bicarbonate solution (1×20 ml), water, 0.5 N sulphuric acid solution (2×20 ml), water. The product is dried over anhydrous sodium sulphate. Ethyl acetate is filtered out and removed in vacuo at 40° C. The residue is dried in vacuo over P$_2$O$_5$. 5.68 g (≈100%) of oil is obtained.

$R_f$=0.42 (benzene-acetone 2:1; Sorbfil plates, Silicagel 8-12 μm, development by UV and chlorine/benzidine).

2) TFA.H-Glu(OBzl)-Asp(OBzl)-OH (II), trifluoracetate of (γ-benzyl)-glutamyl-(β-benzyl)aspartate 5.68 g (≈0.01 mole) of N-tert.butyloxycarbonyl-(γ-benzyl) glutamyl-(β-benzyl) aspartate (I) is dissolved in 20 ml of dichlormethan-trifluoracetic acid mixture (3:1). Two hours later the solvent is removed in vacuo at 40° C. The removal is repeated with another portion of dichlormethan (2×10 ml). The residue is dried in vacuo over NaOH. 5.80 g (≈100%) of oil is obtained. $R_f$=0.63 (n-butanol-pyridine-acetic acid-water, 15:10:3:12).

3) Z-Ala-Glu(OBzl)-Asp(OBzl)-OH (III), N-carbobenzoxyalanyl-(γ-benzyl)-glutamyl-(β-benzyl)aspartate.

5.65 g (0.01 mole) of trifluoracetate of (γ-benzyl)-glutamyl-(β-benzyl)aspartate (II) is dissolved in 10 ml of dimethylformamide and added with 2.80 ml (0.02 mole) of triethylamine and 4.14 g (0.013 mole) of N-oxysuccinimide ester of N-carbobenzoxyalanine. The mixture is stirred for 24 hours at room temperature.

The product is precipitated with 0.5N sulphuric acid solution (150 ml), extracted by ethyl acetate (3×30 ml), washed in 0.5N sulphuric acid solution (2×20 ml), water, 5% sodium bicarbonate solution (1×20 ml), water, 0.5N sulphuric acid solution (2×20 ml), water. The product is dried over anhydrous sodium sulphate. Ethyl acetate is filtered out and removed in vacuo at 40° C. The residue is crystallised in the ethyl acetate/hexane system. The product is filtered and dried in vacuo over P$_2$O$_5$. The yield is 4.10 g (66%). The temperature of melting ($T_{mt}$) equals 154° C.

$R_f$=0.48 (benzene-acetone, 1:1), $R_f$=0.72 (N-butanol-pyridine-acetic acid-water, 15:10:3:12).

4) Z-Ala-Glu(OBzl)-Asp(OBzl)-Arg-OH (IV), N-carbobenzoxyalanyl-(γ-benzyl)glutamyl-(β-benzyl)aspartylarginine 5.0 g (8 mmole) of N-carbobenzoxyalanyl-(γbenzyl)-glutamyl-β-benzyl)aspartate (III) and 1.35 g (10 mmole) of N-oxybenzotriazol is dissolved in 20 ml of dimethylformamide. The mixture is cooled down to 0° C. 2.0 g (10 mmole) of cooled N,N'-dicyclohexylcarbodiimide solution in 5 ml is added, the mixture is stirred for 20 minutes. Then cooled suspension of HCl.H-Arg-OH, 5.00 g (24 mmole) of arginine hydrochloride in 15 ml of dimethylformamide is added. The mixture is stirred at this temperature for 2 hours and left to blend for a night at room temperature. Precipitate of dicyclohexylurea and excessive arginine is filtered out. 0.51 of 2N H$_2$SO$_4$ is poured into the filtrate until yellow precipitate appears. The mixture is left in the refrigerator for a night. Precipitate is dissolved in 100 ml of n-butanol saturated with 2% acetic acid, and several times washed in 2% acetic acid. Organic layer is washed with water until pH value is neutral, and removed in vacuo. The residue is crystallized in diethyl ester, then filtered and dried over P$_2$O$_5$. The yield is 2.5 g (45%).

$R_f$=0.88 (n-butanol-acetic acid-water 4:1:1).

5) H-Ala-Glu-Asp-Arg (SEQ ID NO:1)-OH (V), alanyl-glutamyl-aspartyl-arginine 2.50 g of N-carbobenzoxyalanyl-(γ-benzyl)glutamyl-(β-benzyl)aspartylarginine (III) is hydrated in methanol-water system (5:1) over Pd/C catalyst. Completeness of the deblocking reaction is monitored by TLC in the benzene/acetone (2:1) and acetonitrile/acetic acid/water (5:1:3) systems. When the reaction is over the catalyst is filtered out, the filtrate is removed in vacuo and the residue is crystallised in the water/methanol system. The product is dried in vacuo over KOH. The yield is 1.00 g (70%).

$R_f$=0.59 (acetonitrile-acetic acid-water, 5:1:3). For purification, 250 mg of the substance is dissolved in 4 ml of 0.01% trifluoracetic acid and subjected to HPLC on a reversed phase column measuring 50×250 mm (Diasorb-130-C16T, 7 μm). The employed chromatograph is Beckman System Gold, 126 Solvent Module, 168 Diode Array Detector Module.

Conditions of chromatography A: 0.1% of TFA; B: MeCN/0.1% of TFA; grad. B 0→10% in 100 min. Sample volume is 5 ml, detection is conducted by 215 nm, scanning—by 190-600 nm, flow rate equals 10 ml/min.

The fraction is selected within 49.0-54.0 min. The solvent is removed in vacuo at a temperature not exceeding 40° C. Purification is repeated using HPLC method under same conditions. The fraction is selected within 32-48 min. The solvent is removed, the removal is multiply repeated (5 times) with 10 ml of 10% acetic acid solution. The residue is finally dissolved in 20 ml of deionised water and lyophilised. 110 mg of purified preparation in the form of amorphous odorless white powder is obtained.

6) Analysis of the Finished Product

Content of the active base (peptide) is defined by HPLC on Supelco LC-18-DB column, LC-18-DB 4.6×250 mm, grad. LC-18-DB. A: 0.1% of TFA; B: MeCN/0.1% of TFA; grad. B0→10% in 30 min. The flow rate equals 1 ml/min. Detection by 220 nm, scanning—by 190-600 nm, the sample volume is 20 µl. Peptide content—98.01%;

The amino acid content is defined on an analyser AAA "T-339" Prague after 24 hours hydrolysis in 6 N HCl at 125° C. Glu 1.08; Asp 1.08; Ala 1.00; Arg 1.07;

TLC: individual, $R_f$=0.59 (acetonitrile-acetic acid-water, 5:1:3). Sorbfil plates, Silicagel, developing in chlorine/benzidine;

Moisture content: 8% (gravimetrically, according to the mass loss by drying—20 mg at 100° C.). pH of 0.001% solution: 4.58 (potentiometrically);

Specific rotary power: $[\alpha]_D^{22}$: –24° (c=1, $H_2O$), "Polamat A", Carl Zeiss Jena.

EXAMPLE 2

Effect of the Tetrapeptide on the Course of Experimental Myocardium Infarction in Case of Coronary Artery Vasoligation in Rats The experiment was conducted on 40 white mongrel rats each weighing 180-200 g. The animals were randomly subdivided into two groups, 20 animals in each. Myocardium infarction (MI) was induced by vasoligation of the left coronary artery. Ala-Glu-Asp-Arg tetrapeptide was administered to the animals intraperitoneally in the dose of 0.05 µg per animal in sterile 0.9% NaCl solution three times—in 1, 3 and 5 hours after coronary occlusion. Rats were decapitated in 6 and 24 hours after the surgery. Animals subjected to the surgery, which intraperitoneally received 0.9% NaCl solution, served as the control. MI zone size was identified gravimetrically. Myocardium fragments were fixed for light and electronic microscopy, part of the material was frozen in liquid nitrogen for biochemical studies.

Results of the experiment are displayed in Table 1. The administration of Ala-Glu-Asp-Arg tetrapeptide caused a reliable decrease in mortality rate in rats during the first 24 hours after infarction (45% in the control and 15% in tetrapeptide-treated rats). Histologically this was manifested in a significant reduction of necrosis zones in tetrapeptide-treated animals already during the first hours of the disease development. The analysis of biochemical indices' dynamics showed that the peptide preparation significantly decreased the glucose content in the blood, which was caused by acute myocardium ischemia, by nearly 1.5 times. This is mainly due to the retained normal activity of marker enzymes—lactate dehydrogenase (LDH) and creatinphosphokinase (CPK). The protective effect of the tetrapeptide in this model is also manifested in the maintenance of glycogen content in myocardium tissue, this index being decreased by 3 times in the absence of the preparation's administration.

Ultrastructural changes in the status of cardiomyocytes were studied using the electronic microscope. The study of 180 electronograms revealed an especially pronounced protective effect of the tetrapeptide, judging by the fact that mitochondrias' structure remained intact, in 24 hours since the beginning of MI. Under the preparation's effect the coefficient of mitochondria energy efficiency (the product of mean total quantity of cristas and the total of mitochondria areas in one electronogram in case of pathology to the product of the same indices in normal heart ratio, expressed in percent) significantly increases with respect to the control animals (93.2±2.3 and 41.5±2.4 correspondingly, p<0.05).

Thus, the tetrapeptide reliably reduces ischemic damage of pre-infarction myocardium and stimulates the reparative processes in it, which makes the cardiomyocytes retain their survivability and normalizes their ultrastructure, while the control animals show increasing severity of ischemic damage, which ends up in their death.

EXAMPLE 3

Effect of the Tetrapeptide on the Status of Isolated Heart in Case of Perfusion and Ischemia The experiment was conducted under conditions of perfusion in isolated hearts of 60 male guinea pigs, by Langendorf. The animals were randomly subdivided into several groups, each consisting of 6 animals. Total cardiac ischemia was induced by means of fully tightening the perfusional solution hose for 30 minutes. Then re-perfusion was performed under the same conditions as before ischemia (control group). In experimental animals perfusion was performed together with Ala-Glu-Asp-Arg (SEQ ID NO:1) tetrapeptide in the concentrations of 0.002-0.05 µg/ml. Mechanical contractions were registered, bioptates, weighing approximately 10 mg, were several times taken from the top of the heart, then the content of malon dialdegide (MDA) was identified in them. The hearts in the end of the experiment and partially before ischemia were frozen in liquid nitrogen for ATP, ADP and AMP content identification.

Another experiment was devoted to the study of the tetrapeptide's effect on the restoration of isolated rat heart's ability to contract after a period of ischemia. The study was conducted on 3 groups, 8 animals in each, in case of the additionally strained cardiac muscle working mode, under conditions of induced contraction rhythm and perfusion solution temperature increase up to 37° C.

The results of the experiment are displayed in Tables 2 and 3. The analysis of the received data suggests that the effects of the tetrapeptide on normal and ishemic heart differ. The administration of the tetrapeptide does not influence the status of the normal heart, while in case of ischemia the preparation's introduction into the perfusate in small doses from 0.002 to 0.005 µg/ml favorably influences the cardiac function in case of ischemia. An increase was registered in the power and amplitude of cardiac contractions, as well as a significant increase in macroergic phosphates content, MDA content not differing significantly from the norm. The tetrapeptide's addition into the perfusional solution in the concentration of 0.005 µg/ml caused a reliable improvement of contractive function—the amplitude of contractions increased (up to 75±12% from the initial level, 43±7% in the control). The speed of contraction and relaxation was significantly higher in the experimental animals, the coronary duct was significantly increased up to 10.8±1.6 ml/min as compared to the control animals (8.5±0.4 ml/min, p<0.05).

The other series of experiments conducted on 12 rat hearts was aimed at the study of the tetrapeptide's protective effect in case of its addition into the perfusate in the concentration of 10 ng/ml before the induction of ischemia. Then "severe"

stimulation was conducted (5 Hz frequency) in the heart and contractive activity was estimated. The study of the tetrapeptide's protective effect in case of its administration before induced ischemia showed, that the tetrapeptide in the dose of 0.005 µg/ml restrained the growth of contracture during the period of ischemia and contributed to its reduction in the course of re-perfusion, while the control hearts after stimulation showed no restoration of normal contractive activity in case of re-perfusion, and the contractions were completely terminated already after 5 minutes of re-perfusion. The administration of the tetrapeptide in a very small dose of 0.005 µg/ml preserved the heart, which was on the verge of stopping, from fibrillation and contractive activity decrease, restoring the value of the latter index.

EXAMPLE 4

Effect of the Tetrapeptide on the Course of Adrenalin Dystrophy in Rat Myocardium The experiment was conducted on 30 white mongrel rats with body weight of 180-200 g. The animals were randomly subdivided into three groups, each consisting of 10 animals. Adrenalin dystrophy was induced by administering the fresh adrenalin solution ("Serva", USA) intraperitoneally in the dose of 2 mg/kg. The control animals received 0.9% NaCl solution. Then the experimental animals were in 1 and 5 hours treated with Ala-Glu-Asp-Arg (SEQ ID NO:1) tetrapeptide in the dose of 0.05 µg per animal in sterile 0.9% NaCl solution. In 4 hours since the beginning of the experiment cardiac muscle bioptates weighing approximately 10 mg were taken for the identification of cardiac dehydrogenases activity and glycogen content in the myocardium. In 24 hours the animals were killed by momentary decapitation. Left ventricle fragments were frozen in liquid hydrogen. In cryostatic slices the activity of succinatedehydrogenase (SDH) was histochemically identified, as well as of NADN-dehydrogenase (NADN-DH), lactatedehydrogenase and glycogen content.

The study results are displayed in Tables 4 and 5.

The studies showed that the administration of the tetrapeptide in conjunction with strong adrenergic stimulation of the myocardium reliably decreases the intensity of POL process, which is one of myocardium damage factors in this model. In 24 hours after the induction of myocardium dystrophy the quantity of diene conjugates in the myocardium of experimental animals was significantly reduced to the norm as compared to the control animals (110±17 and 176±24 mmole/g of tissue correspondingly, p<0.05).

Histochemical study of dehydrogenase activity and glycogen content in the myocardium tissue during the first hours since adrenalin administration (Table 5) revealed, that the tetrapeptide significantly decreases the activity of lactatedehydrogenase, which contributes to acidosis reduction and better maintenance of cardiac muscle under conditions of oxygen shortage. This is confirmed by the retained glycogen amount in the heart of rats, which received the tetrapeptide, as compared to the control animals (0.168±0.021 and 0.112±0.0.17 rel. optic density units correspondingly).

Thus, the administration of Ala-Glu-Asp-Arg (SEQ ID NO:1) tetrapeptide exerts the protective effect with respect to adrenalin influence on enzymatic systems of the organism, which enables to decrease the excessive intensity of lipid peroxidation processes and to reduce the development of small-focus necrobiotic adrenalin myocardial dystrophy.

EXAMPLE 5

Protective Activity of the Tetrapeptide in Experimental Toxicochemical Myocardiopathy in Case of Poisoning by Tetramethyl Thiuram Disulfide The experiment was conducted on 40 white mongrel rats with body weight of 220-230 g. The animals were randomly subdivided into four groups. The intoxication of animals with tetramethyl thiuram disulfide (TMTD) industrial poison was conducted in the form of 20-day course of 5% oil TMTD solution administration in the dose of 25 mg/kg intragastrically. The tetrapeptide was administered during the last 10 days of the experiment intramuscularly in the dose of 0.05 µg per animals in sterile 0.9% NaCl solution. Upon expiry of the indicated terms both the control and experimental animals were killed by momentary decapitation. Myocardium fragments were fixed by 12% formalin solution. Paraphin slices were stained by hematoxylin-eosine, as well as by Van Gison, Brachet, with sudan III, IV. Intact animals served as the control.

The results of the study are displayed in Table 6.

Morphological study revealed the correcting effect of the tetrapeptide in case of animals' poisoning with TMTD industrial poison. The results of histological and morphometrical study showed, that the administration of the tetrapeptide to the intact animals somehow increased the filling of the myocardium, as well as the volume of cardiomyocytes' nuclei (by 11% and 14% correspondingly). Against the background of TMTD damaging influence this preparation significantly contributed to the restoration of nuclear-cytoplasmatic ratio (from 0.16±0.02 in conditions of intoxication up to 0.28±0.03), reduced stroma volume (from 0.218±0.01 $cm^3$/$cm^3$ in intoxicated animals up to 0.180±0.02 $cm^3$/$cm^3$), increased the volume of parenchyma up to the normal values.

Thus, the study showed that the tetrapeptide restores the myocardium structure and normalizes the main volume ratios in the cardiac muscle of intoxicated animals. This is an evidence of the preparation's positive effect on the accelerated restoration of the cardiac function in case of intoxication by industrial poison.

EXAMPLE 6

Effect of the Tetrapeptide on the Development and Outcome of Chlorine-Calcium Arrhythmia in Rats The experiment was conducted on 60 white mongrel rats with body weight of 180-200 g. The animals were randomly subdivided into 6 groups, each consisting of 10 animals. The rats were narcotized with urethane and received 220 mg/kg of 10% $CaCl_2$ solution. Ala-Glu-Asp-Arg tetrapeptide was administered to the animals intraperitoneally, once, in the doses of 0.05-1.0 µg/kg in sterile 0.9% NaCl solution.

The results of the study, displayed in Table 7, show, that 0.2 µg/kg is the most efficient dose. The tetrapeptide decreases the death rate of the animals, significantly reduces the frequency of ventricle fibrillation development, increases the frequency of sinus rhythm restoration after the first $CaCl_2$ administration, as well as a tolerable arrhythmogen dose. The preparation in the doses of 0.2 µg/kg and 0.5 µg/kg contributed to the normalization of the frequency of heart contractions (FHC): in this case bradicardia rats showed an FHC increase by 12.3-48.6%, and rats with initial tachycardia showed FHC decrease to the normal limits, caused by the tetrapeptide.

Thus, the administration of Ala-Glu-Asp-Arg (SEQ ID NO:1) tetrapeptide contributes to the normalization of cardiac function in case of arrhythmia.

EXAMPLE 7

Effect of the Tetrapeptide on the Growth of Organotypic Cardiac Culture Explants of Pubertal Rats Cardiac tissue explants (from the left and right ventricles) of pubertal Wistar rats were cultivated in petri dishes with collagen bottom cover. The nutritious medium was composed of 35% Eagle's medium, 35% Hanx solution, 25% calf fetal serum and 5% of chicken embryonic extract with added glucose, insulin, gentamycin and glutamin. Ala-Glu-Asp-Arg (SEQ ID NO:1) tetrapeptide was added into the cultural medium in fixed concentrations, from 0.01 to 20.0 ng per ml of nutritious medium. After 3 days of incubation at the temperature of 37° C. the increase in the area of explants was identified using phase contrast microscope. Biological activity of the preparation was expressed in the change of square index (SI) of the explants cultivated in the medium containing the peptide, as compared to the control.

The results of this experiment are displayed in Table 8, which shows, that Ala-Glu-Asp-Arg tetrapeptide stimulates the growth of organotypic cardiac culture explants in a wide scope of concentrations. In the zone of intense growth under the influence of the tetrapeptide there were found outgoing myocardiocytes with large round nuclei characteristic for immature myocardiocytes, as well as endothelial cells and fibroblasts. Immunohistochemical method of proliferative nuclear antigen (PCNA) detection with subsequent computer analysis of microscopic images revealed, that the enhancement of cell proliferative potential plays the leading role in the effect of Ala-Glu-Asp-Arg (SEQ ID NO:1) tetrapeptide.

Thus, the administration of Ala-Glu-Asp-Arg (SEQ ID NO:1) tetrapeptide contributes to the accelerated renovation of normal cardiomyocytes population and hence stimulates myocardium tissue function.

EXAMPLE 8

Effect of the Tetrapeptide on Cardiomyocyte Bioenergetics

Cardiomyocytes were extracted from the cardiac muscle of pubertal rats by Vahouny. Oxygen consumption by isolated cardiomyocytes was registered polarographically at the temperature of 30° C. Part of cardiomyocytes suspension was oxygenated by saturation with carbogen for 1-3 hours at room temperature. The other part of suspension was not oxygenated (conditions of moderate hypoxia). Succinate was added in the concentration of $1 \times 10^{-4}$ M, and oxygen consumption stimulation showed the extent of cell bioenergetics damage by hypoxia. The tetrapeptide was introduced into the medium in the concentration of 10 ng/ml.

The study results showed, that the tetrapeptide's administration into the medium normalized the process of succinate oxidation. So, in the conditions of hypoxia the coefficient of breath stimulation (breath rate in the presence of succinate to initial breath rate ratio) made 7.35±0.26, and the administration of the tetrapeptide reduced this index to 1.97±0.26. Meanwhile oxygen consumption was not altered if the tetrapeptide was added into oxygenated cells suspension. It was revealed, that the tetrapeptide's administration into the medium increases $NAD.H_2$ oxidation by cardiomyocytes. Thus, the tetrapeptide normalizes cardiomyocyte bioenergetics in the conditions of oxygen deprivation by selectively inhibiting the oxidation of succinic acid and by contributing to $NAD.H_2$ oxidation.

Additional studies conducted on myocardium slices taken from different animals revealed the inhibiting effect of the tetrapeptide on the activity of succinate dehydrogenase, which presumably underlies the protective influence of the tetrapeptide on respiratory processes in myocardium cells in case of hypoxia.

EXAMPLE 9

Study of Common Toxicity of the Tetrapeptide

Common toxicity of Ala-Glu-Asp-Arg (SEQ ID NO:1) tetrapeptide was studied in compliance with the requirements stated in "Manual for experimental (pre-clinical) study of new pharmaceutical substances" (2000): acute toxicity in case of single administration of the substance, as well as sub-acute and chronic toxicity in case of long-term administration of the tetrapeptide.

The experiment aimed at the study of acute toxicity was conducted on 66 white mongrel male mice with body weight of 20-23 g. The animals were randomly subdivided into 6 equal groups. The substance was administered once, intramuscularly, in 0.25 ml volume, in the doses of 1 mg/kg, 2 mg/kg, 3 mg/kg, 4 mg/kg and 5 mg/kg in sterile 0.9% NaCl solution. The control animals received 0.9% NaCl solution.

The study of sub-acute toxicity was conducted on 60 white mongrel male rats with body weight of 160-240 g. The experimental animals daily, once a day, for 90 days, intramuscularly received the substance in the doses of 1 µg/kg, 0.1 mg/kg, 1 mg/kg in 0.5 ml of 0.9% NaCl solution. The control animals received 0.9% NaCl solution in the same volume. Before the substance's administration, as well as on the $30^{th}$, $60^{th}$ and $90^{th}$ day after the beginning of the course the morphological composition and the properties of the animals' peripheric blood were studied. Upon completion of the experiment the biochemical and coagulological indices of the animals' blood were studied.

The studies of chronic toxicity were conducted for 6 months, basing on the duration of the recommended clinical administration of the preparation, on 96 male guinea pigs with body weight of 300-340 g. The experimental animals received the tetrapeptide daily, once a day, intramuscularly, for 6 months in the doses of 1 µg/kg, 0.1 mg/kg and 1 mg/kg in 0.5 ml of 0.9% NaCl solution. The control animals received 0.9% NaCl solution in the same volume and by the same schedule. Common methods were used for the identification of the quantity of erythrocytes, hemoglobin, reticulocytes, thrombocytes, leukocytes, as well as of the leukocyte formula, erythrocyte sedimentation rate (ESR) and erythrocyte resistance in the peripheric blood of the animals. Alongside with this general protein content in the blood serum was estimated by Lowry's method, as well as of potassium and sodium using the method of plasma spectrophotometry. After the completion of the experiment the pathomorphological study of the brain and spinal cord, spinal cord ganglia, thyroid gland, parathyroid glands, adrenal glands, testis, pituitary gland, heart, lungs, aorta, liver, kidney, urinary bladder, pancreas, stomach, small intestine, large intestine, thymus, spleen, lymph nodes and bone marrow was conducted.

Acute toxicity study revealed, that a single administration of the tetrapeptide to the animals in the dose, 5000 times exceeding the therapeutic one, recommended for clinical administration, does not cause toxic reactions, which proves the wide therapeutic diapason of the substance.

The study of the tetrapeptide's sub-acute and chronic toxicity shows the absence of side effects in case of long-term administration of the substance in the doses, which exceed the therapeutic ones by 100-1000 times. The study of the tetrapeptide's effect on the morphological composition of guinea pig blood revealed the increase in leukocyte quantity in 3 and 6 months after the beginning of the substance's administration (Table 9). The other indices reflecting the morphological composition of the animals' blood remained largely unchanged. No significant influence of the preparation on ESR was registered, as well as on erythrocyte resistance and on biochemical indices of the blood serum.

The assessment of the animals' general status, as well as of the morphological and biochemical indices of the peripheric blood, morphological status of internal organs, the status of cardiovascular and respiratory system, of liver and kidney functions showed no pathologic changes in the organism.

The absence of general toxicity allows to recommend the pharmaceutical substance, containing the tetrapeptide as an active peptide agent, for clinical studies.

TABLE 1

| | Control | | Tetrapeptide | |
|---|---|---|---|---|
| Index | 6 hours | 24 hours | 6 hours | 24 hours |
| Necrosis zone size, % of ventricle mass | 44.1 ± 1.7 | 56.2 ± 1.4 | 38.1 ± 1.8* | 49.6 ± 1.6* |
| Death rate | 7 | 2 | 2 | 1 |
| Content in the blood serum: | | | | |
| glucose, mmole/l | 4.55 ± 0.23 | 3.9 ± 0.15 | 3.12 ± 0.09 | 3.01 ± 0.11 |
| LDH, nmole/s · 1 | 311 ± 11 | 252 ± 19 | 309 ± 16 | 201 ± 15* |
| CPK, nmole/s · 1 | 1326 ± 64 | 1073 ± 24 | 961 ± 52* | 923 ± 38 |
| Glycogen content in the myocardium, g/kg of the tissue | 0.36 ± 0.07 | 0.38 ± 0.06 | 1.05 ± 0.12* | 1.18 ± 0.12** |

*$p < 0.05$ as compared to the control;

**$p < 0.01$ as compared to the control.

TABLE 2

| Indices and experimental conditions | Before ischemia | Re-perfusion | |
|---|---|---|---|
| | | 15 min | 30 min |
| Amplitude of contractions, % of initial | | | |
| control | 100 | 72 ± 9 | 75 ± 8 |
| tetrapeptide (0.002 µg/ml) | 100 | 70 ± 13 | 81 ± 16 |
| tetrapeptide (0.005 µg/ml) | 100 | 89 ± 6* | 93 ± 5* |
| tetrapeptide (0.01 µg/ml) | 100 | 61 ± 4* | 64 ± 3* |
| tetrapeptide (0.05 µg/ml) | 100 | 38 ± 13* | 32 ± 9* |
| MDA, nmole/g of tissue | | | |
| control | 230 ± 12 | 195 ± 23 | 201 ± 19 |
| tetrapeptide (0.002 µg/ml) | 225 ± 23 | 216 ± 5 | 220 ± 12 |
| tetrapeptide (0.005 µg/ml) | 168 ± 25* | 231 ± 7 | 186 ± 10 |
| tetrapeptide (0.01 µg/ml) | 203 ± 18 | 248 ± 8 | 220 ± 9 |
| tetrapeptide (0.05 µg/ml) | 156 ± 28* | 264 ± 13* | 252 ± 11* |
| Energy charge (µmole of adenosine phosphates/g of tissue) | | | |
| control | 7.56 ± 0.25 | — | 3.32 ± 0.16 |
| tetrapeptide (0.002-0.005 µg/ml) | 7.68 ± 0.21 | — | 6.01 ± 0.23* |
| tetrapeptide (0.05 µg/ml) | 7.78 ± 0.14 | — | 2.98 ± 0.35 |

*$p < 0.01$ as compared to the control.

TABLE 3

| | Contraction parameters for 10 min re-perfusion | | | | |
|---|---|---|---|---|---|
| Animal group | Amplitude of contractions, % of init. | Extent of contracture, mm | Max. speed of contraction, % of init. | Max. speed of relaxation, % of init. | Coronary duct, ml/min |
| Control | 43 ± 7 | 1.2 ± 0.5 | 42 ± 7 | 46 ± 5 | 8.5 ± 0.4 |
| Tetrapeptide | | | | | |
| 0.005 µg/ml | 75 ± 12* | 1.3 ± 0.4 | 56 ± 10* | 69 ± 8* | 10.8 ± 1.6* |
| 0.05 µg/ml | 36 ± 10* | 2.5 ± 0.3 | 28 ± 7* | 28 ± 6* | 9.6 ± 0.7 |

*$p < 0.05$ as compared to the control.

TABLE 4

| Animal group | Organ | Diene conjugates content, nmole/g of tissue | Malon dialdegide content, nmole/g of tissue |
|---|---|---|---|
| Control | heart | 112 ± 21 | 169 ± 19 |
| | liver | 125 ± 18 | 186 ± 27 |
| Adrenalin | heart | 176 ± 24* | 153 ± 14 |
| | liver | 146 ± 34 | 356 ± 54* |
| Adrenalin + tetrapeptide | heart | 110 ± 17** | 173 ± 25 |
| | liver | 92 ± 11** | 270 ± 56* |

*$p < 0.05$ as compared to the control;
**$p < 0.01$ as compared to the index after adrenalin administration.

TABLE 5

| | Experimental conditions | | |
|---|---|---|---|
| Studied parameter | Control | Adrenalin | Adrenalin + tetrapeptide |
| Glycogen content, rel. optical density unit | 0.143 ± 0.016 | 0.112 ± 0.0,17* | 0.168 ± 0.021** |
| Enzyme activity in the myocardium tissue: | | | |
| LDH, rel. optical density unit | 0.142 ± 0.006 | 0.193 ± 0.10* | 0.154 ± 0.011** |
| SDH, rel. optical density unit | 0.275 ± 0.021 | 0.297 ± 0.012 | 0.284 ± 0.013 |
| NADN-DH, rel. optical density unit | 0.334 ± 0.009 | 0.329 ± 0.014 | 0.344 + 0.019 |

*$p < 0.05$ as compared to the control;
**$p < 0.01$ as compared to the index after adrenalin administration.

TABLE 6

| Index | Control | Tetrapeptide | TMTD | TMTD + tetrapeptide |
|---|---|---|---|---|
| Cardiomyocyte nuclei volume, μm$^3$ | 336.2 ± 5.4 | 386.2 ± 2.1* | 276.3 ± 15.9* | 365.4 ± 13.8** |
| Stroma volume, cm$^3$/cm$^3$ | 0.143 ± 0.03 | 0.159 ± 0.05 | 0.218 ± 0.01* | 0.180 ± 0.02** |
| Vessels volume, $V_{cap}/V_{cmc}$ | 0.06 ± 0.008 | 0.08 ± 0.006* | 0.11 ± 0.03* | 0.07 ± 0.02** |
| Parenchyma volume, cm$^3$/cm$^3$ | 0.81 ± 0.03 | 0.82 ± 0.04 | 0.76 ± 0.02* | 0.83 ± 0.02** |
| Nuclear-cytoplasmatic ratio | 0.29 ± 0.02 | 0.40 ± 0.04* | 0.16 ± 0.02* | 0.28 ± 0.03** |

*$p < 0.01$ as compared to the control;
**$p < 0.01$ as compared to the index in the animals not treated with the tetrapeptide;
$V_{cap}/V_{cmc}$ - capillaries to cardiomyocytes volume ratio.

TABLE 7

| Group, preparation, dose | Death after the first arrhythmogen administration, abs. % | Frequency of sinus rhythm restoration after the first CaCl$_2$ administration, % | Frequency of ventricle fibrillation development in the course of the experiment, % | Maximum tolerable arrhythmogen dose, mg/kg |
|---|---|---|---|---|
| Control (CaCl$_2$) | 7 (70) | 20.0 | 60.0 | 220 |
| Tetrapeptide in concentration: | | | | |
| 0.05 μg/kg | 5 (50) | 27.0 | 60.3 | 220 |
| 0.1 μg/kg | 5 (50) | 29.6 | 45.8 | 220 |
| 0.2 μg/kg | 3 (30) | 49.0* | 35.2* | 440 |
| 0.5 μg/kg | 4 (40) | 39.5* | 39.1* | 440 |
| 1.0 μg/kg | 6 (60) | 16.3 | 43.6 | 220 |

*$p < 0.05$ as compared to the control.

TABLE 8

| Index | Concentration of the tetrapeptide, ng/ml | | | | | | | |
|---|---|---|---|---|---|---|---|---|
| | 0.01 | 0.05 | 0.1 | 0.5 | 1.0 | 2.0 | 10.0 | 20.0 |
| SI, % with respect to the control | 10 | 20* | 22* | 20* | 15* | 20* | 27* | 8 |

*p < 0.05 as compared to the control.

TABLE 9

| | Administration of the tetrapeptide (1 µg/kg) | | | |
|---|---|---|---|---|
| | 3 months | | 6 months | |
| Index | Control (n = 24) | Tetrapeptide (n = 24) | Control (n = 24) | Tetrapeptide (n = 24) |
| Erythrocytes, $\times 10^{12}$/l | 5.3 ± 0.6 | 5.4 ± 0.2 | 5.4 ± 0.3 | 5.2 ± 0.4 |
| Hemoglobin, g/l | 14.2 ± 1.4 | 13.8 ± 1.2 | 14.5 ± 1.3 | 14.2 ± 0.6 |
| Reticulocytes, % | 1.3 ± 0.07 | 1.2 ± 0.07 | 1.1 ± 0.05 | 1.3 ± 0.08 |
| Thrombocytes, $\times 10^9$/l | 143.7 ± 7.9 | 143.6 ± 8.4 | 144.5 ± 8.6 | 144.9 ± 9.8 |
| Leukocytes, $\times 10^9$/l | 9.4 ± 0.5 | 11.2 ± 0.8* | 9.6 ± 0.5 | 11.9 ± 0.5* |
| Stab neutrophils, % | 0.31 ± 0.04 | 0.27 ± 0.07 | 0.33 ± 0.04 | 0.36 ± 0.05 |
| Segmented neutrophils, % | 45.8 ± 2.1 | 44.9 ± 2.5 | 46.2 ± 3.5 | 43.4 ± 3.2 |
| Eosinophils, % | 0.69 ± 0.05 | 0.64 ± 0.04 | 0.72 ± 0.04 | 0.75 ± 0.08 |
| Basophils, % | 0.61 ± 0.04 | 0.69 ± 0.05 | 0.72 ± 0.03 | 0.71 ± 0.05 |
| Monocytes, % | 2.5 ± 0.02 | 2.4 ± 0.03 | 2.6 ± 0.06 | 2.5 ± 0.05 |
| Lymphocytes, % | 48.9 ± 2.5 | 50.7 ± 2.4 | 51.3 ± 2.7 | 52.7 ± 2.2 |
| ESR, mm/hour | 1.69 ± 0.05 | 1.87 ± 0.07 | 2.01 ± 0.05 | 2.05 ± 0.04 |
| Erythrocyte resistance, % NaCl | | | | |
| maximum | 0.41 ± 0.02 | 0.430.04 | 0.42 ± 0.04 | 0.44 ± 0.04 |
| minimum | 0.32 ± 0.05 | 0.33 ± 0.02 | 0.34 ± 0.04 | 0.35 ± 0.05 |
| General protein in the blood serum, g/l | 72.9 ± 3.1 | 72.6 ± 3.3 | 73.1 ± 3.4 | 73.1 ± 3.6 |
| Sodium in the blood serum, mmole/l | 153.9 ± 5.7 | 154.8 ± 6.8 | 155.5 ± 6.2 | 154.6 ± 6.9 |
| Potassium in the blood serum, mmole/l | 5.1 ± 2.3 | 5.3 ± 1.8 | 5.2 ± 2.1 | 5.4 ± 2.2 |

*P < 0.05 as compared to the control.

The invention claimed is:

1. Tetrapeptide alanyl-glutamyl-aspartyl-arginine with general formula: Ala-Glu-Asp-Arg (SEQ ID NO: 1).

2. A pharmaceutical composition comprising tetrapeptide Ala-Glu-Asp-Arg (SEQ ID NO: 1) and a pharmaceutically acceptable carrier.

3. A method of restoring myocardial function in a patient with diminished myocardial function comprising administering an effective amount of tetrapeptide Ala-Glu-Asp-Arg (SEQ ID NO: 1) to the patient.

4. The method of claim 3, wherein the tetrapeptide is administered orally or parenterally.

5. The method of claim 3, wherein the tetrapeptide reduces ischemic damage of pre-infarction myocardium.

6. The method of claim 3, wherein the tetrapeptide increases the contractive function of the heart during ischemic reperfusion.

7. The method of claim 3, wherein the tetrapeptide restrains the growth of contracture during ischemia.

8. The method of claim 3, wherein the tetrapeptide exerts a cardioprotective effect against adrenaline induced damage.

9. The method of claim 3, wherein the tetrapeptide exerts a cardioprotective effect against intoxication induced by industrial poison.

10. The method of claim 3, wherein the tetrapeptide normalizes cardiac function in case of arrhythmia.

11. The method of claim 3, wherein the tetrapeptide accelerates renovation of normal cardiomyocytes population.

12. The method of claim 3, wherein the tetrapeptide normalizes cardiomyocytes bioenergetics under hypoxic conditions.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: Synthetic peptide

<400> SEQUENCE: 1

Ala Glu Asp Arg
1
```